(12) United States Patent
Shanmugham

(10) Patent No.: US 8,956,159 B2
(45) Date of Patent: Feb. 17, 2015

(54) ORTHODONTIC DEBONDING TOOL, TOOL INSERT AND METHOD FOR REMOVING ORTHODONTIC BRACKETS

(76) Inventor: Chitra Shanmugham, Ontario (CA)

(*) Notice: Subject to any disclaimer, the term of this patent is extended or adjusted under 35 U.S.C. 154(b) by 0 days.

(21) Appl. No.: 13/510,001

(22) PCT Filed: Oct. 28, 2011

(86) PCT No.: PCT/CA2011/001199
§ 371 (c)(1),
(2), (4) Date: May 15, 2012

(87) PCT Pub. No.: WO2012/061923
PCT Pub. Date: May 18, 2012

(65) Prior Publication Data
US 2013/0216970 A1  Aug. 22, 2013

(30) Foreign Application Priority Data

Nov. 9, 2010  (CA) .................................. 2720442

(51) Int. Cl.
*A61C 3/03* (2006.01)
*A61C 3/06* (2006.01)
*A61C 5/00* (2006.01)
*A61C 7/02* (2006.01)
*A61C 7/16* (2006.01)

(52) U.S. Cl.
CPC .. *A61C 7/023* (2013.01); *A61C 7/16* (2013.01)
USPC ................................ 433/118; 433/166; 433/3

(58) Field of Classification Search
CPC .............. A61C 1/07; A61C 3/00; A61C 3/02; A61C 3/025; A61C 3/03; A61C 3/06; A61C 3/12; A61C 7/023
USPC ............... 433/118–119, 86, 3, 125, 165–166, 433/142; 128/200.16; 451/165, 910; 81/432; 606/79, 82, 85
See application file for complete search history.

(56) References Cited

U.S. PATENT DOCUMENTS 3,086,288 A * 4/1963 Balamuth et al. ............ 30/277.4
5,263,957 A * 11/1993 Davison ........................ 606/169
(Continued)

FOREIGN PATENT DOCUMENTS

| CA | 1252636 | 4/1989 |
| WO | 2004086998 | 10/2004 |
| WO | WO 2010/122288 | * 10/2010 ............. A61B 17/16 |

OTHER PUBLICATIONS

International Search Report and Written Opinion for PCT/CA2011/001199 mailed Feb. 7, 2012.
(Continued)

*Primary Examiner* — Heidi M Eide
(74) *Attorney, Agent, or Firm* — James P. Muraff; Neal, Gerber & Eisenberg, LLP

(57) ABSTRACT

A tool bit for removing orthodontic brackets includes a handpiece-engaging portion, a shaft portion, a curved portion and a working end portion. The curved portion provides sufficient offset to present the end portion in a substantially co-planar relationship with a tooth surface. The working end portion includes at least one beveled cutting surface for cutting away the adhesive and at least one blunt/flat polishing surface for polishing away any residual adhesive that may remain after bracket removal. The tool bit may also include a cooling fluid delivery port. Edges of the beveled surfaces may be serrated. Beveled surfaces and the top surface may be coated with an abrasive material such as diamond grit. These cutting surfaces are used to cut through the adhesive layer bonding the bracket to the tooth. The tool has a blunt/flat second edge surface for polishing away any remaining adhesive after bracket removal.

11 Claims, 2 Drawing Sheets

(56) References Cited

U.S. PATENT DOCUMENTS

| | | | | |
|---|---|---|---|---|
| 5,695,510 A | * | 12/1997 | Hood | 606/169 |
| 6,379,371 B1 | * | 4/2002 | Novak et al. | 606/169 |
| 2002/0119421 A1 | * | 8/2002 | Gratz | 433/142 |
| 2004/0126735 A1 | * | 7/2004 | Hickok et al. | 433/119 |

OTHER PUBLICATIONS

International Preliminary Report on Patentability for PCT/CA2011/001199 mailed May 14, 2013.

* cited by examiner

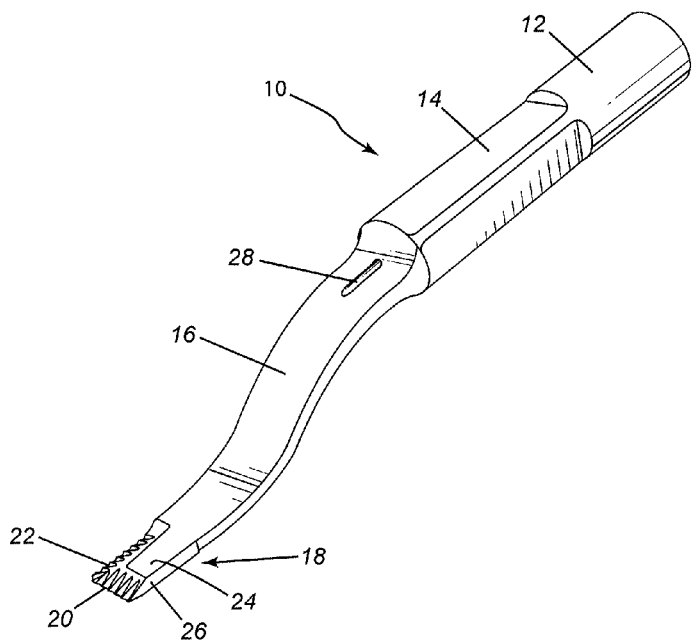
FIG. 1
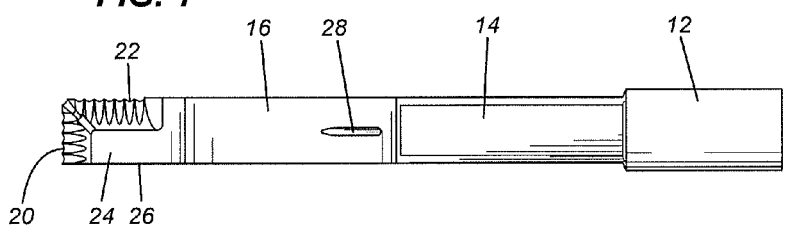
FIG. 2
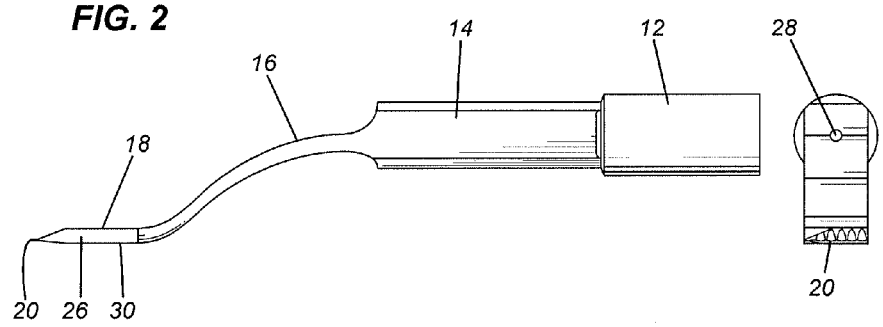
FIG. 3
FIG. 5

ORTHODONTIC DEBONDING TOOL, TOOL INSERT AND METHOD FOR REMOVING ORTHODONTIC BRACKETS

CROSS-REFERENCE TO RELATED APPLICATIONS

This is a national stage patent application of PCT/CA2011/001199, filed on Oct. 28, 2011, that claims priority from Canadian Patent Application No. 2,720,442, filed Nov. 9, 2010, both of which are incorporated by reference in their entirety.

TECHNICAL FIELD

The present invention relates generally to dentistry and, in particular, to techniques and devices for removal of orthodontic brackets.

BACKGROUND

Debonding pliers, manual tools currently in practice, are available for the removal of orthodontic brackets. When the material of the brackets was only metal, there was sufficient structural integrity in the bracket to withstand a torque that these traditional tools applied in order to shear the adhesive bond between the bracket and the tooth. However, the removal of metal brackets sometimes resulted in enamel fracture.

Today in orthodontics, there is an increasing demand for relatively invisible aesthetic brackets. These brackets are generally made of polycarbonates or ceramics where the latter are either monocrystalline or polycrystalline. Since adhesion of brackets is considered semi-permanent in orthodontics, bond strength should be sufficiently high to resist accidental debonding during the entire course of treatment but low enough so that excessive force is not needed when debonding the brackets after treatment. The major concern during bracket debonding is the risk of enamel damage, as reported by the European Journal of Orthodontics in 2008.

With the introduction of ceramic, plastic, ICE, and other more fragile materials for orthodontic brackets, these manual tools requiring torque proved problematic. For example, using these prior-art tools increased the risk of enamel fracture and/or bracket fracture.

There are some solutions proposed in the literature to deal with these types of orthodontic brackets. For example, an article by Krell, K V, Courey, J M & Bishara, S E, 1993 'Orthodontic bracket removal using conventional and ultrasonic debonding techniques, enamel loss, and time requirements", *American Journal of Orthodontics and Dentofacial Orthopedics*, vol. 108, no. 3, pp. 262-266, discusses the use of the already existing, plain ultrasonic chisels. However, the use of these instruments raises concerns about possible damage to tooth surfaces as well as fracture of the brackets.

Embodiments disclosed herein provide a tool, tool insert and method for removing orthodontic brackets that obviate or mitigate at least some of the aforementioned disadvantages.

SUMMARY

The present invention provides an orthodontic debonding tool, tool bit (or tool insert) for said tool, and a related method of debonding orthodontic brackets. This invention constitutes an innovative solution to the problem of removing orthodontic brackets and the related problem of removing excess adhesive from the teeth without damaging the enamel of the teeth while also reducing chair-side time.

In accordance with an aspect of the present invention, a tool bit (or tool insert) for removing orthodontic brackets comprises a handpiece-engaging portion (or handpiece-interface portion), a curved portion connected to the handpiece-engaging portion, and a working end connected to the curved portion. The working end has at least one beveled cutting surface for cutting an adhesive that bonds the orthodontic brackets to respective teeth and at least one blunt or flat polishing surface for polishing away any residual adhesive that remains after the orthodontic brackets have been removed. Cutting surfaces and the blunt polishing surface may be coated with abrasive material such as diamond grit. Edges of the beveled cutting surfaces may be serrated.

In accordance with another aspect of the present invention, an orthodontic debonding tool comprises an ultrasonic handpiece, e.g. a piezoelectric hand piece and a tool bit connected to the ultrasonic handpiece. The tool bit includes a curved portion connected to the handpiece-engaging portion, and a working end portion connected to the curved portion. The working end portion includes a front edge having a first beveled surface and a first side edge having a second beveled surface.

In accordance with yet another aspect of the present invention, a method for debonding orthodontic brackets that are bonded to teeth with an adhesive entails connecting a tool bit to an ultrasonic handpiece, ultrasonically vibrating the tool bit, cutting the adhesive using a cutting surface of the tool bit to remove the brackets, and polishing away any remaining adhesive using a flat or blunt surface of the tool bit.

Other aspects of the invention will become apparent with reference to the following description and drawings.

BRIEF DESCRIPTION OF THE DRAWINGS

The present invention will be further understood from the following detailed description with reference to the drawings in which:

FIG. 1 is a perspective view of a tool bit for removing orthodontic brackets in accordance with an embodiment of the present invention;

FIG. 2 is a top plan view of the tool bit shown in FIG. 1;

FIG. 3 is a side elevation view of the tool bit shown in FIG. 1;

FIG. 5 is a frontal elevation view of the tool bit shown in FIG. 1;

DETAILED DESCRIPTION OF EMBODIMENTS

Figure 4:
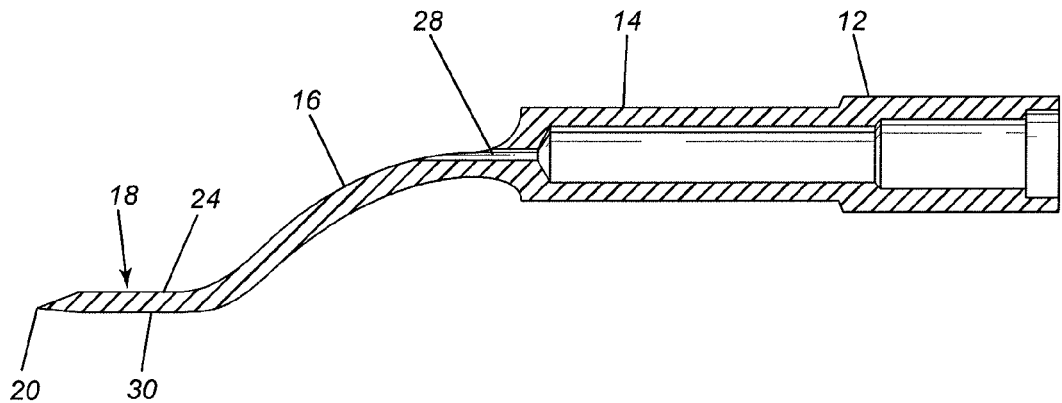
FIG. 4 is a cross-sectional view of the tool bit shown in FIG. 1.

FIGS. 1 to 5 illustrate a novel tool bit for removing orthodontic brackets in accordance with an embodiment of the present invention. The tool bit 10, which is also referred to herein as a "tool tip", "tool insert" or simply "insert", includes a handpiece-engaging portion 12, a shaft portion 14, a curved portion 16, and a working end portion 18. The handpiece-engaging portion 12 may be connected to the handpiece by threads, quick-connect or any other suitable means of mechanical connection. The curved portion 16 provides sufficient offset to present the end portion in a substantially co-planar relationship with a tooth surface. The working end portion 18 (or "shank") has at least one cutting surface for cutting or abrading away adhesive that bonds the bracket to the tooth and at least one polishing surface for polishing away any residual adhesive that may remain after the bracket has been removed. In the particular embodiment depicted in these figures, the working end portion 18 includes a number of cutting edges or cutting surfaces designed to cut away the adhesive that bonds the orthodontic brackets to the surface of the teeth. In the preferred embodiment depicted in the figures, the working end portion 18 includes a front edge 20, a first side edge 22, a top (upper) surface 24, and a second side edge 26. The front edge 20 and the first side edge 22 are designed to cut and abrade the adhesive. The second side edge 26 is a blunt surface designed to polish the tooth to remove any remaining adhesive after the bracket has been detached from the tooth.

As shown in these figures, the tool bit also includes a cooling fluid delivery port 28 (i.e. a cooling fluid delivery conduit) for conveying water (or any other biocompatible cooling fluid) as part of a cooling fluid delivery system. The cooling fluid delivery port (conduit) directs cooling fluid (e.g. water) onto the cutting surfaces/edges of the working end of the tool bit to cool and clean the working end of the tool bit during operation. The fluid flow in the embodiment depicted in the drawings may be varied from its current design. In other words, the flow direction may be changed, internal or external fluid sources may be employed, the flow rate may be increased or decreased, and any additive may be added to the fluid to increase, e.g. to improve the cooling efficiency or for other reasons.

Figure 6:
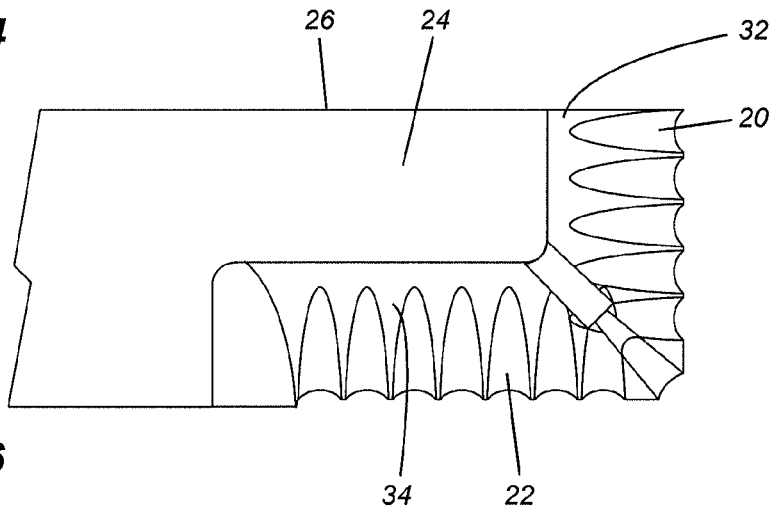
FIG. 6 is a partial top plan view of the end portion of the tool bit shown in FIG. 2.

Referring to FIG. 6, the working end portion 18 is shown in greater detail. In a preferred embodiment, the tool bit 10 includes a front beveled cutting surface 32 and a side beveled cutting surface 34. These surfaces may be coated with an abrasive particle such as diamond grit. The front beveled cutting surface 32 may have, as shown, a serrated front edge 20. The side beveled cutting surface 34 may also have a serrated side edge 22. The front edge 20 and the first side edge 22 are the edges of abrasive-coated beveled surfaces 32 and 34, respectively. As shown by way of example in FIG. 6, these surfaces 32 and 34 have serrated edges. In preferred embodiments, beveled surfaces 32 and 34 and the top (upper) surface 24 are coated with an abrasive material such as, for example, diamond grit, tungsten carbide particles or any other hard abrasive particle. Abrasive beveled surfaces 32 and 34 provide for abrasive cutting, i.e. by abrasion. In a preferred embodiment, the abrasive material includes diamond grit. A diamond particle size of 40 microns (i.e. a grit mesh size of 400) is believed to work well, although diamond grit of other particle sizes may be utilized. In the preferred embodiment, the second side edge 26 (which is not serrated in the illustrated embodiment) is also coated with an abrasive material such as diamond grit (although in other embodiments, it need not be coated with an abrasive). Other suitable types of abrasives or grit may be utilized.

Figure 7:
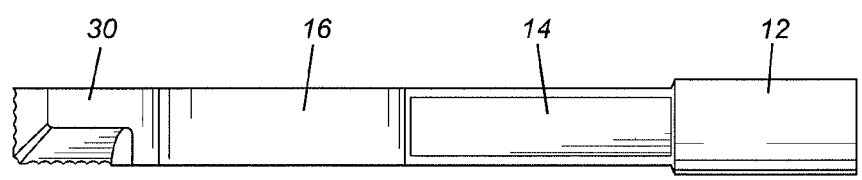
FIG. 7 is a bottom plan view of the tool bit shown in FIGS. 1.
Figure 8:
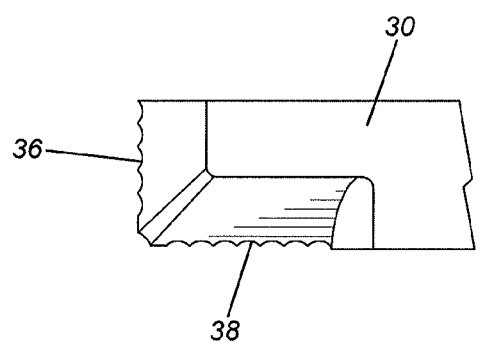
FIG. 8 is a partial bottom plan view of the end portion of the tool bit shown in FIG. 7.

Referring to FIGS. 7 and 8, there is illustrated in a bottom plan view and partial view the tool bit of FIGS. 1 to 6. FIGS. 7 and 8 show a flat and smooth undersurface 30 with adjacent serrated, abrasive-coated, beveled surfaces 36 and 38. The smooth flat undersurface 30 is masked during the abrasive coating process so no abrasive material is adhered to this undersurface 30. The undersurface 30 is made smooth to avoid damaging the enamel of the tooth when the tool is used to pry the orthodontic bracket from the tooth. In other words, this undersurface 30 provides relief to a tooth surface from abrasive beveled surfaces 36 and 38 used to remove the adhesive layer bonding the bracket to the tooth. Thus, the tooth surface (enamel) is safely distanced from the abrasive surfaces. In other embodiments, the cutting surfaces and the blunt polishing surface may be coated with abrasive material such as diamond grit or any other suitable abrasive material.

In operation, the tool bit 10 is inserted into a handpiece of an ultrasonic unit, e.g. a piezoelectric handpiece, although the bit could, in other embodiments, be shaped and dimensioned to connect to an air scaler, electric scaler, sonic device, or any other mechanical, electrical or electro-mechanical patient-application device. The ultrasonic unit transmits vibrations through the handpiece to the tool bit 10 to facilitate a cutting action at the front and first side edges 20 and 22. Abrasive beveled edges 32, 34, 36 and 38 wear away the adhesive layer bonding the bracket to the tooth, while the smooth undersurface 30 ensures that the tooth enamel is protected from the abrasive surfaces. The blunt side surface 26 (which may or may not be coated with an abrasive) may be used for polishing the tooth to remove any remaining adhesive from the surface of the tooth after the orthodontic bracket has been removed. The combination of the two sets of serrated edges 32 and 34 together with 36 and 38 provide a fine edge for entry into the adhesive layer.

The tool bit 10 may be made of surgical stainless steel (e.g. stainless steel 316L). Alternatively, the tool bit 10 may be made of titanium or any other suitable material that is capable of transmitting the ultrasonic vibrations from the handpiece to the working end 18 of the tool bit 10. The handpiece-engaging portion 12 (i.e. handpiece-interfacing portion) may be adapted to fit any type of handpiece. The fluid delivery port may also be eliminated where an external fluid delivery system can be attached to the tool bit and/or handpiece.

In the preferred embodiment, the cutting surfaces/edges 20, 22 are serrated. As shown in the FIG. 6, these serrations may be parallel to a longitudinal axis of the shank 18 of the tool bit 10. This "rake angle" (i.e. the angle between the serrations and the longitudinal axis) in the illustrated embodiment is thus zero (since the forward-facing serrations are parallel to the longitudinal axis). The rake angle may be varied to achieve other effects.

Furthermore, the number of serrations may be varied from what is depicted by way of example in the figures.

In another embodiment, the tool bit 10 may also be constructed without any serrations at all. In that case, all cutting action is performed by the abrasive particles. In such an embodiment, the abrasive grit size may be varied (e.g. increased). Furthermore, in another embodiment, the tool bit may have only a subset of the serrated edges that are shown in the preferred embodiment, e.g. only the front edge 20 or only the first side edge 22.

In another embodiment, the "shank angle", i.e. the angle of the shank 18 relative to the handpiece-engaging portion 12 and the shaft portion 14, may also be varied. In the illustrated embodiment, the shank angle is zero since the shank is parallel to the handpiece-engaging portion 12 and the shaft portion 14. Other shank angles may be desirable for achieving different effects. Likewise, the shank-to-tip angle may be varied from what is shown by way of example in the illustrated embodiments to achieve different effects.

It should also be appreciated that the lengths and widths of the handpiece-engaging portion 12, shaft portion 14, and working end portion (shank) 18, as well as their respective ratios, may all be varied.

A right-handed tool bit is depicted in the drawings. As shown, the serrated edge 22 runs along the right side of the tool bit 10. A left-handed tool bit may be constructed with a serrated edge along the left side of the tool bit (for left-handed dentists).

Another aspect of the invention is a novel orthodontic debonding tool incorporating the novel tool bit described above. The debonding tool (to be attached to the ultrasonic hand piece available in the market) includes an ultrasonic handpiece for ultrasonic vibration of the novel tool bit. The novel tool bit comprises (as described above), the tool-engaging portion, shaft portion, and working end. As noted above, the working end, or shank, includes one or more cutting surfaces and/or edges that cut away the adhesive to detach the brackets from the teeth. These cutting surfaces/edges may be abrasive-coated and/or serrated, as described above. At least one surface of the tool bit is a polishing surface. In the preferred embodiment, as depicted in the drawings, the flat smooth bottom surface 30 protects the adjacent enamel of the tooth when the tool is used to pry an orthodontic bracket from the tooth.

Yet another aspect of the invention is a novel method of debonding orthodontic brackets using the novel tool bit described above. This method entails connecting a tool bit to an ultrasonic handpiece and then ultrasonically vibrating the tool bit (activating the handpiece or an ultrasonic unit connected to the handpiece). This causes the tool bit to oscillate at an ultrasonic frequency. Optionally, the frequency may be controlled using a controller. The method then entails cutting adhesive (that bonds the orthodontic brackets to the teeth) using one or more cutting surfaces and/or cutting edges of the tool bit to thereby remove the brackets. Once the brackets have been removed, there will usually be some residual adhesive on the teeth. The method thus entails a further step of polishing away any remaining adhesive using a smooth surface of the same tool bit. Thus, the invention provides a single tool bit that can be used to both remove (detach) the bracket and also polish the tooth. This invention not only reduces the likelihood of enamel fracture and/or of a bracket breaking during removal but also reduces the total time required to remove the brackets from the teeth. This also reduces the discomfort for the patient. As will be appreciated, the quicker and more effective bracket removal is highly advantageous to both dentist and patient alike. By facilitating the task of removing the orthodontic brackets, this tool may enable the dentist to assign the task to the orthodontic hygienist (once approved by the clinic or if permissible under local dentistry regulations) as most orthodontic hygienists are already familiar with similar equipment for their hygiene practice. The tip depicted by way of example in the drawings was designed for and successfully tested with a piezoelectric ultrasonic device providing linear erasure-type motion although other types of motion may be employed. For example, in another embodiment, a magnetostrictive ultrasonic device providing an elliptical figure-eight motion may be employed.

The foregoing embodiments are presented by way of example to illustrate particular ways of implementing this invention. Persons of ordinary skill in the art having read this disclosure will recognize that numerous modifications, refinements, variations, alterations and adaptations may be made to the particular embodiments described above without departing from the scope and spirit of the inventive concepts presented in the present specification. The scope of the exclusive right sought by the Applicant is therefore intended to be defined solely by the claims.

The invention claimed is:

1. A tool bit for removing orthodontic brackets, the tool bit comprising:
   a handpiece-engaging portion defining a first longitudinal axis;
   a curved portion connected to the handpiece-engaging portion; and
   a working end portion connected to the curved portion, wherein the working end portion defines a second longitudinal axis that is offset from the first longitudinal axis, the working end portion having:
   a front beveled cutting surface substantially perpendicular to the second longitudinal axis for cutting an adhesive that bonds the orthodontic brackets to respective teeth;
   a side beveled cutting surface substantially parallel to the second longitudinal axis for cutting the adhesive; and
   a blunt side surface substantially parallel to the second longitudinal axis for polishing away any residual adhesive that remains after the orthodontic brackets have been removed, wherein the blunt side surface is parallel to and spaced-apart from the side beveled cutting surface and wherein the front beveled cutting surface is perpendicular to the side beveled cutting surface.

2. The tool bit as claimed in claim 1 wherein the front beveled cutting surface has a serrated front edge and wherein the side beveled cutting surface has a serrated side edge.

3. The tool bit as claimed in claim 1 wherein the front and side beveled cutting surfaces are coated with an abrasive material.

4. The tool bit as claimed in claim 1 wherein the front and side beveled cutting surfaces are coated with diamond grit.

5. The tool bit as claimed in claim 1 wherein the working end portion includes an upper surface that is coated with abrasive material.

6. The tool bit as claimed in claim 1 comprising a biocompatible cooling fluid delivery port.

7. An orthodontic debonding tool for removing orthodontic brackets, the tool comprising:
   an ultrasonic handpiece; and
   a tool bit connected to the ultrasonic handpiece by a handpiece-engaging portion of the tool bit, wherein the handpiece-engaging portion defines a first longitudinal axis, the tool bit having:
   a curved portion connected to the handpiece-engaging portion; and
   a working end portion connected to the curved portion, wherein the working end portion defines a second longitudinal axis that is offset from the first longitudinal axis, the working end portion having:
   a front beveled cutting surface substantially perpendicular to the second longitudinal axis for cutting an adhesive that bonds the orthodontic brackets to respective teeth;
   a side beveled cutting surface substantially parallel to the second longitudinal axis for cutting the adhesive; and
   a blunt side surface substantially parallel to the second longitudinal axis for polishing away any residual adhesive that remains after the orthodontic brackets have been removed, wherein the blunt side surface is parallel to and spaced-apart from the side beveled cutting surface and wherein the front beveled cutting surface is perpendicular to the side beveled cutting surface.

8. The orthodontic debonding tool as claimed in claim 7 wherein the tool bit comprises a biocompatible cooling fluid delivery port.

9. The orthodontic debonding tool as claimed in claim 7 further comprising a biocompatible cooling fluid delivery system attached to the tool bit.

10. The orthodontic debonding tool as claimed in claim 7 wherein the front beveled cutting surface and the side beveled cutting surface each have serrated edges.

11. The orthodontic debonding tool as claimed in claim 7 wherein the front and side beveled cutting surfaces are coated with an abrasive material.

\* \* \* \* \*